(12) United States Patent
Msika et al.

(10) Patent No.: US 7,511,010 B2
(45) Date of Patent: Mar. 31, 2009

(54) PHARMACEUTICAL OR COSMETIC COMPOSITION AND USE OF A PKC INHIBITOR WITH AN MMP INHIBITOR FOR INHIBITING LANGERHANS' CELL MIGRATION

(75) Inventors: Philippe Msika, Paris (FR); Nathalie Piccardi, Saint Egreve (FR); Antoine Piccirilli, Epernon (FR)

(73) Assignee: Laboratoires Expanscience, Courbevoie (FR)

( * ) Notice: Subject to any disclaimer, the term of this patent is extended or adjusted under 35 U.S.C. 154(b) by 0 days.

(21) Appl. No.: 10/416,464

(22) PCT Filed: Nov. 14, 2001

(86) PCT No.: PCT/FR01/03568

§ 371 (c)(1),
(2), (4) Date: Aug. 25, 2003

(87) PCT Pub. No.: WO02/40004

PCT Pub. Date: May 23, 2002

(65) Prior Publication Data

US 2004/0067910 A1    Apr. 8, 2004

(30) Foreign Application Priority Data

Nov. 14, 2000  (FR) .................................. 00 14607

(51) Int. Cl.
*A61K 38/00* (2006.01)
*A61K 31/13* (2006.01)
(52) U.S. Cl. ............................................ 514/2; 514/669
(58) Field of Classification Search ................. 514/158, 514/2, 669
See application file for complete search history.

(56) References Cited

U.S. PATENT DOCUMENTS

| | | | |
|---|---|---|---|
| 5,891,906 A | 4/1999 | Driedger et al. | |
| 5,981,491 A | 11/1999 | Baxter et al. | |
| 6,040,152 A | 3/2000 | Kupfer et al. | |
| 6,846,812 B2 * | 1/2005 | Dalko et al. | 514/171 |

FOREIGN PATENT DOCUMENTS

| | | | |
|---|---|---|---|
| WO | WO 93/23075 A1 | 11/1993 | |
| WO | WO 98/43959 A1 | 10/1998 | |
| WO | WO 99/43805 A1 | 9/1999 | |
| WO | WO 00/03734 A1 | 1/2000 | |
| WO | WO 00/62789 A1 | 10/2000 | |

OTHER PUBLICATIONS

Lebre, M.C. et al., "Inhibition of contact sensitizer-induced migration of human Langerhans cells by matrix metalloproteinase inhibitors", *Archives of Dermatological Research* (1999), 291 (July and August), pp. 447-452.*

Bheekha-Escura, R., "Pharmacologic Regulation of Histamine Release by the Human Recombinant Histamine-Releasing Factor," *Journal of Allergy and Clinical Immunology* (1999), pp. 937-943, vol. 103, No. 5 (USA).

Burnham, K., "Requirements for Langerhans' Cell Depletion Following in vitro Exposure of Murine Skin to Ultraviolet-B," *Immunology* (1993), pp. 627-632, vol. 79, No. 4, Oklahoma (USA).

Chang, Y. et al., "Regulation of Matrix Metalloproteinase-2 Production by Cytokines and Pharmacological Agents in Human Pulp Cell Cultures," *Journal of Endodontics* (2001), pp. 679-682, vol. 27, No. 11 (USA).

Fisher, G. J. et al., "Differential Expression of Conventional and Nonconventional Protein Kinase C Isozymes in Normal and Psoriatic Skin," *Journal of Investigative Dermatology* (1992), p. 635.

Halliday, G.M. et al., "Protein Kinase C Transduces the Signal for Langerhans' Cell Migration from the Epidermis," *Immunology* (1993), pp. 621-626, vol. 79 (Sydney, Australia).

Liesveld et al., "Studies of Progenitor Cell Transendothelial Migration: Effects of Cytokine Mediators, Signal Transduction Inhibitors, and Gelatinases," *Blood* (2000), p. 151b, vol. 96, No. 11 Part 2 (San Francisco, California).

Newman, J., "A Stereoselective Synthesis of D-*erythrol*-Sphingosine," *Journal of the American Chemical Society* (1973), pp. 4098-4099, vol. 95, No. 12.

* cited by examiner

*Primary Examiner*—Raymond J. Henley, III
*Assistant Examiner*—Alicia Hughes
(74) *Attorney, Agent, or Firm*—Foley & Lardner LLP

(57) ABSTRACT

The invention concerns a pharmaceutical or cosmetic composition, characterised in that it comprises at least a compound for inhibiting Langerhans' cell migration, said active compound being selected in the group consisting of protein kinase C (PKC) inhibiting compounds, matrix metalloprotease (MMP) inhibiting compounds, and combinations thereof, and at least a pharmaceutically or cosmetically acceptable carrier. Said composition enables to inhibit considerably Langerhans' cell migration induced by the presence or an allergenic agent.

3 Claims, 1 Drawing Sheet

Figure 1:
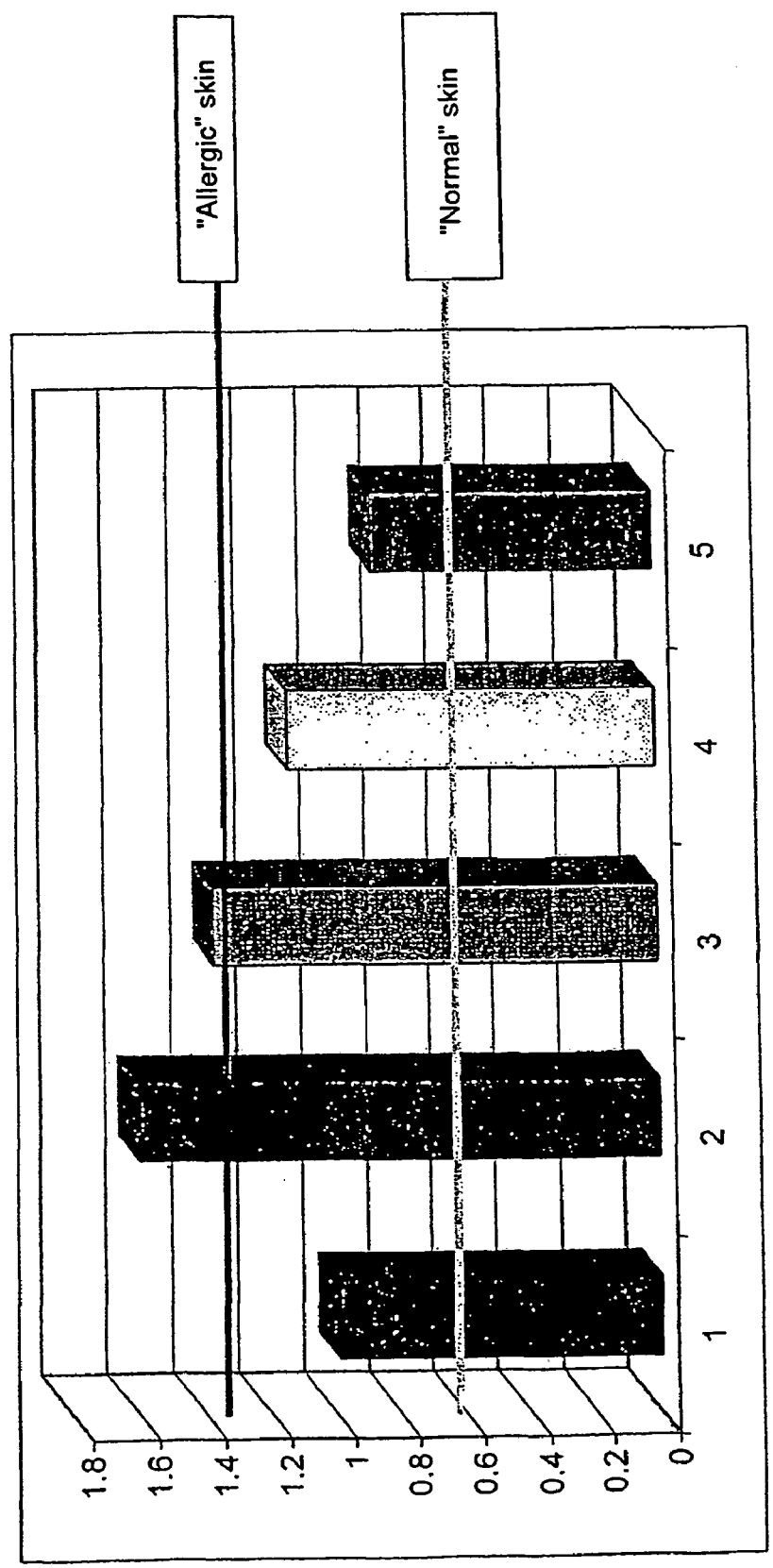

PHARMACEUTICAL OR COSMETIC COMPOSITION AND USE OF A PKC INHIBITOR WITH AN MMP INHIBITOR FOR INHIBITING LANGERHANS' CELL MIGRATION

The present invention relates to a pharmaceutical or cosmetic composition, and also to the use of at least one active compound for inhibiting the migration of cells involved in the immune and/or inflammatory and/or irritative response, such as dermal dendrocytes, monocytes, lymphocytes, and more particularly Langerhans cells.

One of the main functions of the skin is to protect the body against attacks from the outside environment. This protection is provided in large part through the cooperation of cells present in the skin, these being cells which are capable, in the presence of a harmful agent, of generating an inflammatory and/or immune response directed against the harmful agent. They are dendritic cells, epidermal Langerhans cells (LCs) and dermal dendrocytes, monocytes, lymphocytes, keratinocytes, mastocytes and vascular endothelial cells.

LCs are dendritic cells derived from the spinal cord which resides in the nonlymphoid tissues, such as the skin and the mucous membranes (mouth, lungs, bladder, rectum, vagina). In the skin, the LCs intercalate between the epidermal keratinocytes in the suprabasal position. In terms of ultrastructure, they are characterized by the presence of a specific organelle of membrane origin, the Birbeck granule. In immunohistochemical terms, LCs express in particular the CD1a molecule and the class II Major Histocompatibility Complex molecules.

LCs play a determining role in immunity, as antigen-presenting cells. Specifically, experiments carried out in mice demonstrate that LCs capture the antigens present in the epidermis and migrate toward the lymphoid tissues draining the skin, where they present the antigen to T cells. Initiation of the immune response to the skin depends on the ability of the LCs to leave the epidermis in order to migrate to the proximal lymph nodes. Various factors can influence this migration: the expression of adhesion molecules, the extracellular matrix proteins, haptens, cytokines, etc. However, the mechanisms involved in LC migration are not yet entirely elucidated. In particular, before reaching the lymph nodes, LCs must not only cross the dermoepidermal junction (DEJ), but also make themselves a path through the dermal extracellular matrix (ECM). The DEJ is mainly composed of laminin 5, of type IV and VII collagen, of nidogen and of perlecan. The ECM which surrounds the dermal fibroblasts essentially contains type I and III collagens.

Pathological conditions of the dermatological type can also be observed as resulting from LC migration subsequent to capture of a surface antigen.

In atopic eczema, the LCs are capable of attaching IgEs at the surface and of inducing a pathological immune response.

In contact eczema, the LCs play a central role since they capture and process the antigen before presenting it to T lymphocytes. This T lymphocyte will keep it in the memory and the immune reaction will be triggered at the second contact.

Given the above, it was therefore highly desirable to be able to modify the migratory ability of LCs, in order to attempt to modify the induction of the immune and/or inflammatory reaction.

It has now been found, entirely surprisingly and unexpectedly, that some compounds make it possible to spectacularly inhibit Langerhans cell migration induced by the presence of an allergenic agent.

The present invention thus relates to a pharmaceutical or cosmetic composition, characterized in that it comprises at least one active compound for inhibiting Langerhans cell migration, said active compound being chosen from the group consisting of protein kinase C (PKC) inhibitors, matrix metalloprotease (MMP) inhibiting compounds, and combinations thereof, and at least one pharmaceutically or cosmetically acceptable excipient.

According to the invention, the term "protein kinases C" or "PKCs" is intended to mean the enzymes which catalyze a phosphorylation reaction on the cell substrate.

When they are activated, PKCs phosphorylate specific serine or threonine residues on protein substrates, which vary according to cell type. In many cells, PKC activation increases the transcription of specific genes.

Protein kinases C (PKCs) are proteins encoded by a family of genes (11 different isoforms). It is in particular known that these proteins are involved in the extracellular signal transduction mediated by growth factors and cytokines, and also by a certain number of other biological molecules. Protein kinase β2 (PKC-β2) appears to be expressed specifically by epidermal LCs.

Any compound known to those skilled in the art to inhibit the phosphorylation activity of PKCs can thus be used as a PKC-inhibiting compound according to the present invention. Mention may, for example, be made of the polypeptides described in application WO 99/43805 (Incyte Pharma Inc.).

In particular, the active compound is a PKC-inhibiting compound chosen from the group consisting of nonspecific PKC inhibitors, inhibitors specific for the isoform PKC-β2, and combinations thereof.

More particularly, the active compound is a PKC-inhibiting compound chosen from the group consisting of phenol and polyphenol compounds, procyanidins (catechins, epicatechins, etc.), alpha-amyrin, lupeol, lupeol linoleate, sterols, stanols, triterpenic alcohols and hydrogenated homologs thereof, antibiotics such as staurosporin or Ro-318425 (or 2-(8)-(aminomethyl)-6,7,8,9-tetrahydropyridol(1,2-a)-indol-3-yl)-3-(1-methylindol-3-ylmaleimide, HCl) as marketed by the company Calbiochem, compounds which act by competition with physiological PKC activators, such as diacylglycerol or phorbol ester, cutaneous lipids of the (lyso) sphingolipid type, lysophospholipids such as ceramides and pseudoceramides, or sphingosine and phytosphingosine, and the derivatives, precursors, analogs and homologs of these compounds, of natural or synthetic origin.

According to the invention, the term "phenol and polyphenol compounds" is intended to mean simple phenols, benzoquinones, phenolic acids, acetophenones, phenylacetic acids, hydroxycinnamic acids, coumarins and isocoumarins, chromones, naphthoquinones, xanthones, anthraquinones, flavonoids, lignans and neolignans, lignins, chalcones, dihydrochalcones, aurones, flavones, flavonols, dihydroflavonols, flavanones, flavanols, flavandiols or leucoanthocyanidins, anthocyanidins, isoflavonoids, biflavonoids, proanthocyanidins and tannins which are condensed.

According to the invention, the term "sterols" is more particularly intended to mean sterol, i.e. the perhydro-1,2-cyclopentanophenanthrene compound having a hydroxyl group at position 3, and the analogs of sterol of general formula (I) below.

Thus, preferably, the sterols which can be used according to the invention correspond to the general formula:

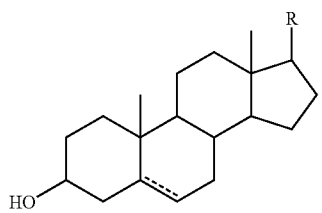

(I)

in which the unsaturation represented as a dotted line at position 5 corresponds to the unsaturation in the case of sterols, R represents a linear or branched hydrocarbon-based chain which may or may not be unsaturated, comprising from 1 to 25 carbon atoms. In particular, R is chosen from the group consisting of $C_1$-$C_{12}$ alkyl groups, $C_1$-$C_8$ alkoxy groups, $C_2$-$C_8$ alkenyl groups, $C_2$-$C_8$ alkynyl groups, $C_3$-$C_8$ cycloalkyl groups, halogenated $C_2$-$C_8$ alkenyl groups, and halogenated $C_2$-$C_8$ alkynyl groups. The term "halogenated" denotes one or more halogen substituents, namely one or more chlorine, fluorine, bromine or iodine atom(s). Among the sterols which may advantageously be used according to the invention, mention may in particular be made of β-sitosterol, α-sitosterol, γ-sitosterol, stigmasterol or, alternatively, campesterol, and mixtures thereof. For example, β-sitosterol can be used in the form of the product known as "Ultra" (mainly comprising β-sitosterol) as marketed by the company Kaukas. In the case of use of a mixture of sterols, mention may, for example, be made of the product known as "Generol" comprising mainly β-sitosterol (approximately 50% by weight), stigmasterol and campesterol, as marketed by the company Henkel or else the product "Primal" from the company Kaukas.

Among the triterpenic alcohols which may advantageously be used according to the invention, mention may in particular be made of β-amyrin, erythrodiol, taraxasterol, cycloartenol, 24-methylene-cycloartanol, lupeol, lanosterol and mixtures thereof.

According to the invention, the term "hydrogenated homologs" of a triterpenic alcohol is intended to mean the corresponding triterpenic alcohol compound(s) in which the unsaturated bond(s) possibly present has (have) been hydrogenated (i.e. converted to a saturated bond) according to methods well known to those skilled in the art.

Even more particularly, the active compound is a PKC-inhibiting compound corresponding to the general formula

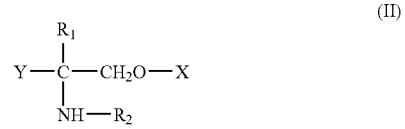

(II)

in which:

$R_1$ represents a hydrogen atom or a linear or branched hydrocarbon-based chain having from 1 to 40 carbon atoms, in particular from 8 to 36, and more particularly from 16 to 20 carbon atoms, which may comprise one or more double bonds and which may comprise one or more hydroxyl substituents;

$R_2$ represents a hydrogen atom or a group of formula Z—CO— where Z represents:

(u) a linear or branched hydrocarbon-based chain having from 1 to 40 carbon atoms, in particular from 16 to 36, and more particularly from 20 to 34 carbon atoms, which may comprise one or more double bonds and which may comprise one or more hydroxyl substituents; or (v) a group $R_6$—CO—O-A- where $R_6$ represents a linear or branched hydrocarbon-based chain having from 1 to 40 carbon atoms, in particular from 8 to 38, and more particularly from 18 to 34 carbon atoms, which may comprise one or more double bonds and which may comprise one or more hydroxyl substituents, and where A represents a linear or branched hydrocarbon-based chain having from 1 to 40 carbon atoms, in particular from 16 to 38, and more particularly from 24 to 36 carbon atoms, which may comprise one or more double bonds and which may comprise one or more hydroxyl substituents;

X represents a hydrogen atom, a monosaccharide residue or oligosaccharide residue, in particular a galactose residue, the sulfogalactose group, phosphorylcholine or the group of formula (GalNAc)(Sia)Gal-Glc-; and Y represents a hydrogen atom or a group of formula $R_3$—W—CHOH— where $R_3$ represents a linear or branched hydrocarbon-based chain having from 1 to 40 carbon atoms, in particular from 8 to 36, and more particularly from 14 to 18 carbon atoms, which may comprise one or more double bonds; and where W represents:

(i) a group of formula —CH=CH—;

(ii) a group of formula —$CH_2$—CH($OR_4$)— where $R_4$ represents a hydrogen atom or a group $R_5$—CO— with $R_5$ representing a linear or branched hydrocarbon-based chain having from 1 to 40 carbon atoms, in particular from 8 to 36, and more particularly from 14 to 18 carbon atoms, which may comprise one or more double bonds and which may comprise one or more hydroxyl substituents; or (iii) a group —$CH_2$—$CH_2$.

Even more particularly, the active compound is a PKC-inhibiting compound chosen from the group consisting of sphingolipids and lysophospholipids, such as those cited in the table below:

TABLE 1

Sphingolipid and lysosphingolipid structures

SPHINGOLIPIDS

Structure: (long-chain ceramide structure with OH, CH₂O—X, NH₂, C=O groups)

| | |
|---|---|
| X = H— | Ceromide |
| X = Galactose- | Galactocerebroside |
| X = Sulfogalatose- | Sulfotide |
| X = GotNAc\Got—Gic—/Sia | GM$_2$ |
| X = Phosphorylcholine- | Sphingomyelin |

LYSOSPHINGOLIPIDS

Structure: (long-chain lysosphingolipid structure with OH, CH₂O—X, NH₃⁻ groups)

| | |
|---|---|
| X = H— | Sphingosine |
| X = Galactose- | Psychosine (Galactosylsphingosine) |
| X = Sulfogalatose- | Lysosulfotide (Sulfogalactosylsphingosine) |
| X = GotNAc\Got—Gic—/Sia | Lyso GM$_2$ |
| X = Phosphorylcholine- | Lysosphingomyelin |

As a PKC-inhibitor compound, mention may also, more particularly, be made of cutaneous lipids of the sphingolipid or lysophospholipid type.

As sphingolipids, mention may be made of those among the most elementary, such as sphingosine (D-erythro-1,3-dihydroxy-2-amino-4-trans-octadecene) and isomers thereof, or phytosphingosine (D-ribo-1,3,4-trihydroxy-2-aminooctadecane) and isomers thereof; but also, lysosphingolipids (including lysosulfatide and psychosine), sulfogalactosylsphingosine, sphinganine (2-amino-1,3-octadecanediol) and sphingomyelins.

As phospholipids, mention may be made of those among the families of phosphatidylamino alcohols and phosphatidyl polyols. The phosphatidylamino alcohol group comprises in particular phosphatidylethanolamines (or phosphatidylcolamines), phosphatidylcholines, phosphatidylserines and N-acylphosphatidylethanolamines. As regards the phosphatidyl polyol group, it comprises phosphatidylcholinositols, diphosphoinositides, lysodiphosphoinositides, phosphatidyl glycerols and cardiolipids.

As a PKC-inhibiting compound, mention may also more particularly be made of ceramides, in particular the ceramides of the intercorneocyte cement of the epidermis and also the ceramide precursors, mainly sphingosine and phytosphingosine.

In general, the ceramides can be synthesized chemically (reference is in particular made to pseudoceramides), may be of animal origin (relatively high concentrations of sphingolipids are present in the mammalian brain and vertebral column), may be of plant origin (mainly cerebrosides and other glycosylated sphingolipids) or else may be derived from yeast (stereochemical configuration identical to that of the ceramides naturally present in human skin).

The ceramides of the intercorneocyte cement of the epidermis can be separated using conventional methods (thin layer chromatography) into six fractions, corresponding to compounds which differ by the nature of the fatty acids and the nature of the base involved (sphingosines, which are unsaturated, or phytosphingosines, which are saturated). Table 2 below illustrates the respective structures present in these fractions, according to the classification of Werts and Downing. Fraction 6 can, itself, be subdivided, by more refined methods, into two entities: ceramides 6a and 6b.

TABLE 2
The six main fractions of epidermal ceramides
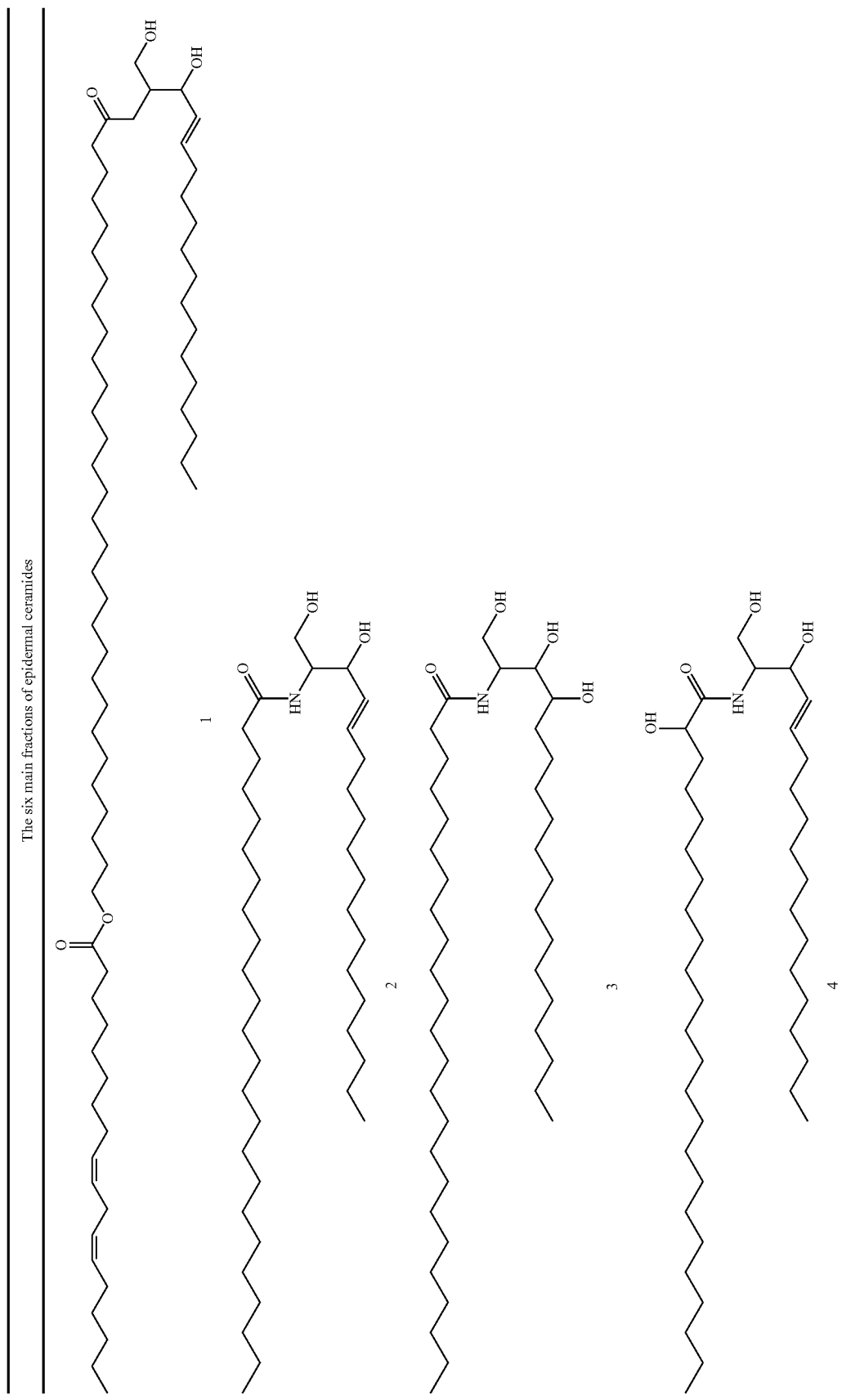

TABLE 2-continued
The six main fractions of epidermal ceramides
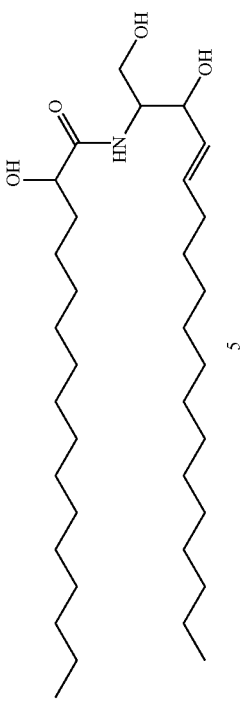
5
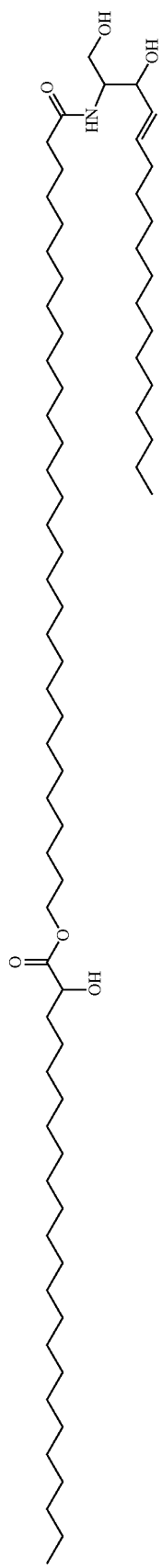
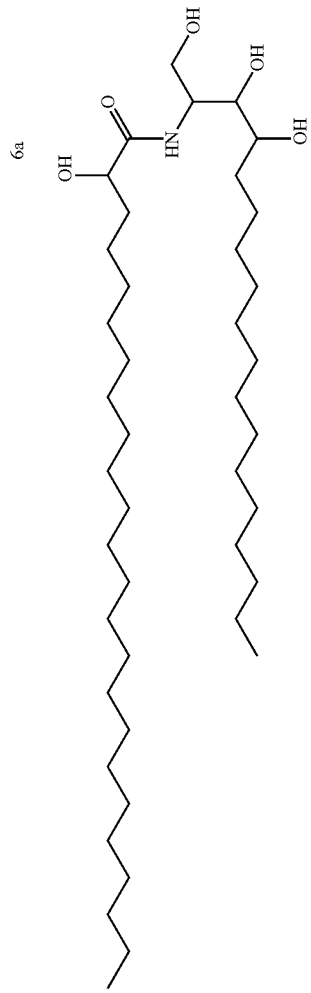
6a
6b Thus, the ceramides 1, the least polar, comprise an entirely specific structure which is found in ceramide 6a: a long-chain omega-hydroxy acid amidating the base, and attached, at its omega end, via an ester bond, to another fatty acid (O-acyl-ceramides). In the case of fraction 1, the fatty acids linked to the sphingosine are essentially C24, C26, C30, C32 or C34, which can be saturated (as represented in FIG. 5 for a C30), monoethylenic (mainly for C30, C32 and C34) or diethylenic (C32 and especially C34). As regards the fatty acid attached to the omega end of the preceding one, it is, largely predominantly for the ceramides 1, linoleic acid; the essential role in the hybrid barrier function of the epidermis is well known.

Fraction 2, which has a more conventional structure (sphingosines or dihydrosphingosines linked, via an amide bond, to a fatty acid, mainly C20 to C28), is the most abundant.

Fraction 3 is quite similar, the difference relating to the nature of the base, which, in this case, is essentially represented by saturated phytosphingosines.

Fractions 4 and 5 are essentially characterized by the presence of alpha-hydroxy acids linked to a sphingosine.

Fraction 6b is close to fractions 4 and 5, comprising an alpha-hydroxy acid, but linked to a saturated phytosphingosine.

Fraction 6a, like the ceramide 1, comprises the characteristic motif which is found only in epidermal ceramides, i.e. the ester bond between the hydroxyl in the omega-position of a fatty acid linked to a sphingosine, and the carboxylic group of a terminal fatty acid which, this time, is not linoleic acid, but an alpha-hydroxy acid.

Phytoceramides (ceramides based on phytosphingosine), synthetic cholesterol ceramides, and galacto- or glucocerebrosides should also be mentioned.

Finally, among the PKC-inhibiting compounds which can be used according to the present invention, sphingosine is present naturally in the skin and plays, inter alia, an important role in the barrier function of the stratum corneum, as a precursor of sphingolipids (ceramides and sphingoglycolipids). It may be derived from a biological source, such as extracts of bovine brains, or via the synthetic pathway, using serine, as described, for example, in the article by Newman, J. Am. CHEM., 95 (12): 4098 (1973). Mention may more particularly be made of the isomeric forms of sphingosine: D-erythro, L-threo, L-erythro and D-threo. The D-erythro form is the form most commonly present in nature.

According to the present invention, the PKC-inhibiting compounds which can be used, as active compounds for inhibiting Langerhans cell migration, comprise the isomers, the derivatives (salts, complexes, etc.), the analogs, the homologs, the precursors and the metabolites of the PKC-inhibiting compounds described above.

According to the invention, the expression "matrix metalloprotease (MMP) inhibiting compounds" is intended to mean any compound known to those skilled in the art for its ability to inhibit the activity of extracellular matrix degradation by MMPs.

MMPs constitute a family of zinc-dependent enzymes (currently more than about twenty have been identified and characterized) which have a very conserved structure and which possess the ability to degrade the components of the extracellular matrix. They are classified, depending on the nature of their substrate, as collagenases, gelatinases and stromelysin. They can be synthesized by various cell types in the skin (fibroblasts, keratinocytes, macrophages, endothelial cells, eosinophils, Langerhans cells, etc.). The MMP group thus consists of four subclasses: (1) collagenases, (2) gelatinases, (3) stromelysins and (4) membrane-type MMPs (MT-MMPs). The activity of MMPs can be modulated by naturally present protease inhibitors, such as tissue inhibitors of metalloproteases (TIMPs; in particular TIMP-1 and TIMP-2).

The predominant role of MMPs in the proteolytic remodeling of the extracellular matrix is now clearly established, both in physiological situations (cicatrization, angiogenesis, embryonic development, etc.) and pathological situations (chronic ulcer, photo-induced aging of the skin, tumor cell invasion, etc.).

In particular, the active compound for inhibiting Langerhans cell migration is a compound which inhibits at least one MMP chosen from the group consisting of MMP-1, MMP-2, MMP-3, MMP-7, MMP-9, MMP-13 and MMP-18.

According to the present invention, the expression "MMP-inhibiting compound", as an active compound for inhibiting Langerhans cell migration, is intended in particular to mean tissue inhibitors of metalloproteases (TIMPs), alpha-2-macroglobulin, plasminogen activator inhibitors, zinc chelators, bryostatin-1, antibiotics (doxycyclins, minocyclins, etc.), synthetic or natural peptides having a structure similar to MMP substrates (batimastat, marimastat, etc.), retinoids (in particular nonaromatic retinoids such as retinaldehyde, tretinoin or 9-cis-retinoic acid, vitamin A, monoaromatic retinoids such as etretinate, all-trans-acitretin or motrerinide, and polyaromatic retinoids such as adapalene, tazarotene, tamibarotene or arotinoid methyl sulfone), antioxidants (singlet oxygen scavengers, etc.), anticancer agents (or "antimetastatics"), malt hydrolysates such as Colalift marketed by the company Coletica, extracts of marine algae such as Kelpadelie marketed by the company Secma, extracts of shark cartilage such as the MDI complex marketed by the company Atrium, rice peptides such as, for example, Colhibin marketed by the company Pentapharm, and peptide extracts of lupin.

More particularly, the MMP-inhibiting compound according to the present invention is chosen from the group consisting of the peptide extracts of lupin, or "lupin peptides", such as those described in patent application FR-99 04 875 filed on Apr. 19, 1999, in the name of the company Laboratoires Pharmascience. Mention may in particular be made of the peptide extract described in application FR 99 04875, under the name extract B (LU105).

Finally, it has been noted, entirely surprisingly and unexpectedly, that particularly advantageous results are obtained when the active compound for inhibiting Langerhans cell migration is a combination of at least one PKC-inhibiting compound, such as those described above, with at least one MMP-inhibiting compound, such as those described above.

It has thus been possible to note, as illustrated in the examples below, that such a specific combination advantageously makes it possible to potentiate, or even to provide a synergistic effect of, the respective activities in order to thus obtain a spectacular effect of inhibition of Langerhans cell migration, which can be compared to complete extinction of the immune response of reactive, sensitive and/or allergic skin, i.e. to the obtaining of a normal skin reactivity.

In particular, the concentration of active compound for inhibiting Langerhans cell migration is between approximately 0.001 and approximately 10% by weight, and more particularly between approximately 0.01 and 3% by weight, relative to the total weight of the pharmaceutical or cosmetic composition.

Preferably, the composition according to the invention is characterized in that the PKC-inhibiting active compound is sphingosine and/or isomers thereof, and said MMP-inhibiting compound is a peptide extract of lupin, more preferably the extract B (LU105).

The composition according to the present invention may also comprise at least one pharmaceutically, in particular dermatologically, or cosmetically acceptable excipient. Any excipient suitable for the pharmaceutical forms known to those skilled in the art, for the purpose of topical, oral, enteral or parenteral administration, can be used.

In particular, the excipient may be suitable for obtaining a composition in the form of an oily or aqueous solution, of a water-in-oil emulsion or an oil-in-water emulsion, of a microemulsion, of an oily or aqueous gel, of an anhydrous gel, of a cream, of a lotion, of a spray, of a mask, of a milk, of a dispersion of vesicles, of microcapsules or of micro-particles, or else of gel capsules or of soft gelatin or plant capsules.

Preferably, an excipient suitable for external topical administration is used.

Finally, the composition according to the present invention may also comprise at least one pharmaceutically or cosmetically acceptable adjuvant known to those skilled in the art, such as thickeners, preserving agents, fragrances, dyes, chemical or mineral screening agents, moisturizers, thermal spring waters, etc.

A subject of the present invention is also the use of an active compound chosen from the group consisting of protein kinase C (PKC)-inhibiting compounds, in particular of those described above, matrix metalloprotease (MMP)-inhibiting compounds, in particular described above, and combinations thereof, for preparing a composition intended to inhibit Langerhans cell migration.

The concentration of active compound used according to the invention is between approximately 0.001 and approximately 10% by weight, and more particularly between 0.01 and 3% by weight, relative to the total weight of the pharmaceutical or cosmetic composition.

The composition thus prepared may also comprise at least one pharmaceutically, in particular dermatologically, or cosmetically acceptable excipient, and also at least one adjuvant, as described above.

In particular, the composition prepared by the use according to the invention is intended for the treatment and prevention of allergic reaction of the skin and of the mucous membranes (mouth, lungs, bladder, rectum, vagina), insofar as it makes it possible to reduce an allergic response in particular induced by LC migration.

More particularly, the composition prepared by the use according to the invention is intended for the treatment and prevention of atopic eczema, insofar as it makes it possible to reduce an immune response in particular induced by the migration of LCs which have attached IgEs at the surface.

The composition prepared by the use according to the invention is also intended for the treatment and prevention of contact eczema, insofar as it makes it possible to reduce an immune response in particular induced by capture of an antigen, processing, and presentation of this antigen to T lymphocytes by the LCs.

The composition prepared by the use according to the invention is also intended for the treatment and prevention of sensitive/reactive skin.

The composition prepared by the use according to the invention is also intended for the treatment and prevention of inflammatory dermatoses and/or irritant dermatitis.

It should therefore be noted that the composition described above may advantageously be used as an additional component in a pharmaceutical or cosmetic product or alternatively a fragrance, in particular for external topical use, containing a main active compound which is allergenic in nature. The allergic reaction thereof will thus advantageously be accordingly decreased, or the dose of main active compound which is allergenic in nature may thus even advantageously be increased.

The composition prepared by the use according to the invention is also intended for the treatment and prevention of autoimmune diseases or inflammatory diseases such as psoriasis.

The composition prepared by the use according to the invention is also intended for the prevention of photoimmunosuppression.

Finally, the composition prepared by the use according to the invention is also intended for the prevention of transplant rejection.

The following examples are intended to illustrate the present invention and can in no way be interpreted as being able to limit the scope thereof. FIG. 1 is a histogram illustrating the migratory indices of the LCs measured as described in example 1: 1: control cells; 2: cells sensitized with the hapten DNSB; 3: DNSB+LU105 (5 µg/ml); 4: DNSB+D-sphingosine (2.5 µM); 5: DNSB+D-sphingosine (2.5 µM)+LU105 (5 µg/ml).

EXAMPLE 1

Study of the Activity of a Combination of a PKC Inhibitor with an MMP Inhibitor on the Inhibition of LC Migration 1) Materials and Methods 1.1 Production of Suspension Enriched in LCs Suspensions of epidermal cells were obtained by enzyme treatment (0.05% trypsin, for 18 h at +4° C.) of fragments of normal human skin derived from plastic surgery. The suspensions obtained contain, on average, 2 to 4% of LCs. The production of suspensions containing, on average, 70% of LCs is based on the principle of density gradient centrifugation (Lymphoprep™) and elimination of keratinocytes.

1.2 Preparation of Media

The basic medium chosen for the entire study was RPMI 1640 (Gibco BRL, France).

D-sphingosine was diluted in ethanol so as to obtain a stock solution at $5 \times 10^{-3}$ M. The D-sphingosine was used at a concentration of 2.5 µM, the dilution carried out in RPMI containing 1% of bovine serum albumin (RPMI-BSA).

A peptide extract of lupin was used as MMP inhibitor. It is the peptide extract LU105 from Laboratoires Pharmascience. LU105 was diluted in RPMI-1640 in order to obtain a stock solution at 250 mg/ml.

LU105 was used at a final concentration of 5 µg/ml, the dilution carried out in RPMI-1640. The cells were pre-incubated at 37° C. for 60 min in the presence of LU105, before adding to the medium the hapten DNSB as sensitizing agent.

1.3 Sensitization of the LCs

As sensitizing agent, DNSB (Sigma Aldrich) was used, the soluble form of DNCB (dinitrochlorobenzene), and was solubilized in RPMI-BSA and used at a concentration of 50 µM.

1.4 Migration of the LCs

A two-compartment culture chamber system (Falcon, Becton Dickinson, France) was used. The upper compartment is separated from the lower compartment by a membrane with a porosity of 8 µm, onto which are deposited 50 µg/cm² of Matrigel. The membrane is then covered with proteins, forming a film equivalent to a basal membrane (laminin, collagen IV, nidogen, entactin, heparan sulfate proteoglycans). The cells taken up in the RPMI-BSA medium alone or in the presence of the various products are placed in the upper compartment. Normal human fibroblast culture supernatant is added to the lower compartment. After incubation for 18 h at 37° C., the number of living cells which have crossed the Matrigel and are in the lower compartment is counted under a microscope (the LCs are easily identifiable by their dendritic shape). Each assay is carried out in triplicate.

2) Results 2.1 The results are given in table 3 below, and illustrated by the histogram of FIG. 1.

TABLE 3

| | LC migration index | | | | |
|---|---|---|---|---|---|
| | 1 | 2 | 3 | 4 | 5 |
| Migration index | 1 | 1.61 | 1.38 | 1.15 | 0.88 |

Legend for table 3 and for the histogram of FIG. 1
1: Control cells
2: Cells sensitized with the hapten DNSB
3: DNSB+LU105 (5 µg/ml)
4: DNSB+D-sphingosine (2.5 µM)
5: DNSB+LU105 (5 µg/ml)+D-sphingosine (2.5 µM)

2.2 Migration of the LCs

The results represent the ratio between the number of cells having migrated in the presence of DNSB±D-sphingosine or LU105 or the combination D-sphingosine+LU105 and the number of cells having migrated under the normal conditions (nonsensitized, nontreated control cells). LCs freshly isolated from the epidermis do not have a high migratory capacity. In expressing the results, the migratory capacity of the control (nontreated and nonsensitized) LCs is arbitrarily fixed at 1.

Treatment of the cells with the hapten DNSB significantly stimulated LC migration (increase of 61%) compared to the normal unstimulated cells (control cells).

D-sphingosine at concentrations of 2.5 µM (table 3) significantly inhibits the LC migration induced by DNSB.

In an experiment in which the cells were not brought into contact with the hapten DNSB, but with LU105 alone (three concentrations), no modification of the migration index, compared to the control (nonsensitized and nontreated) cells, was observed. This indicates that, in the absence of stimulation of the LCs, LU105 has no effect on the migration. LU105 (5 µg/ml) significantly inhibits LC migration induced by DNSB.

The combination D-sphingosine+LU105 makes it possible to completely inhibit the effect of DNSB on the LCs, the number of LCs having migrated in the presence of DNSB+ D-sphingosine+LU105 being similar to that of the control (nonsensitized and nontreated) cells. This combination therefore has a potentiating effect on the intrinsic properties of the two products tested.

3) Conclusions

In this study, we have demonstrated, using freshly isolated LCs placed in a two-compartment culture chamber system (allowing cell migration), that D-sphingosine (PKC inhibitor) potentiates the inhibitory effect of LU105 (MMP inhibitor) on the migration of LCs sensitized with the hapten DNSB, and vice versa. Specifically, these two molecules used separately significantly inhibit LC migration. When they are combined, the sensitized LCs have a migratory capacity similar to that of nonactivated LCs. In other words, according to this example, the combination of a PKC inhibitor and an MMP inhibitor makes it possible to completely extinguish the immune response of reactive/sensitive and allergic skin, and therefore to return to a situation of normal skin.

The invention claimed is:

1. A pharmaceutical or cosmetic composition, comprising a combination of at least one D-phytosphingosine and peptide extract of lupin LU 105, and at least one pharmaceutically or cosmetically acceptable excipient.

2. The composition of claim 1, wherein the concentration of said at least one-D-phytosphingosine and said LU 105 is between approximately 0.001 and approximately 10% by weight, relative to the total weight of the pharmaceutical or cosmetic composition.

3. A method for inhibiting Langerhans cell migration comprising administering to a subject in need thereof a composition comprising a combination of active compounds comprising at least one D-phytosphingosine and peptide extract of lupin LU 105.

\* \* \* \* \*